(12) United States Patent
Peat et al.

(10) Patent No.: US 6,478,950 B1
(45) Date of Patent: Nov. 12, 2002

(54) SENSING LIQUIDS IN OIL WELL USING ELECTROCHEMICAL SENSOR

(75) Inventors: Robert Peat, Longcot (GB); Paul Antony Harry Fennell, Didcot (GB)

(73) Assignee: Accentus PLC, Didcot (GB)

( * ) Notice: Subject to any disclaimer, the term of this patent is extended or adjusted under 35 U.S.C. 154(b) by 0 days.

(21) Appl. No.: 09/647,523

(22) PCT Filed: Apr. 20, 1999

(86) PCT No.: PCT/GB99/01200

§ 371 (c)(1),
(2), (4) Date: Oct. 2, 2000

(87) PCT Pub. No.: WO99/56120

PCT Pub. Date: Nov. 4, 1999

(30) Foreign Application Priority Data

Apr. 23, 1998 (GB) .............................................. 9808517

(51) Int. Cl.[7] .............................................. G01N 27/26
(52) U.S. Cl. ........................ 205/775; 204/400; 204/402; 204/415; 205/687; 205/705
(58) Field of Search ................ 204/400, 402, 204/415; 205/775, 687, 705

(56) References Cited

U.S. PATENT DOCUMENTS

| 1,889,889 | A | * | 12/1932 | Ennis |
| 2,084,143 | A | * | 6/1937 | Hummel |
| 3,410,778 | A | * | 11/1968 | Krasberg |
| 3,509,034 | A | * | 4/1970 | Paine |
| 3,655,546 | A | * | 4/1972 | Marovich et al. |
| 4,154,660 | A | * | 5/1979 | Micko |
| 4,624,760 | A | * | 11/1986 | Pottinger et al. |
| 4,655,900 | A | * | 4/1987 | Neti et al. |
| 4,950,378 | A | * | 8/1990 | Nagata |
| 5,162,077 | A | * | 11/1992 | Bryan et al. |
| 5,261,283 | A | * | 11/1993 | Bertinsson et al. |

FOREIGN PATENT DOCUMENTS

| DE | 3822911 | * | 1/1989 |
| EP | 0212038 | * | 3/1987 |
| JP | 2-82147 | * | 3/1990 |

* cited by examiner

*Primary Examiner*—T. Tung
(74) *Attorney, Agent, or Firm*—William H. Holt

(57) ABSTRACT

A sensor module for monitoring chemical properties of oil well fluids comprises at least one electrochemical sensor for a chemcal species, for example to detect pH and chloride ion concentration. A micro-porous barrier separates the electrochemical sensors from the environment of the module, the micro-porous barrier being of a material which is readily wetted by water. Periodic application of a current pulse between the barrier and a counter electrode enables fouling material to be removed from the micron barrier.

6 Claims, 2 Drawing Sheets ately 1.5 V between them for less than one second, sufficient to generate micro-bubbles by electrolysis -->

SENSING LIQUIDS IN OIL WELL USING ELECTROCHEMICAL SENSOR

This invention relates to an electrical sensor which is suitable for sensing properties of liquids, in particular chemical properties, and which can be used in an environment in which it may be exposed to non-aqueous liquids, and to the use of such a sensor in an environment such as an oil well.

Various different electrical sensors are already known, for example glass electrodes for measuring pH, and resistance thermometers for measuring temperature. Glass electrodes are one type of electrochemical sensor; their operation depends upon there being contact between the glass electrode and an aqueous phase, so that problems can arise if such electrodes are used in environment such as an oil well where they may be exposed to non-aqueous liquids. Sensors used in such an environment may also become fouled. Cleaning techniques which are suitable for use at ambient pressures may not be effective at the high pressures experienced at depth in such a well.

According to the present invention there is provided an electrical sensor module, the module comprising at least one electrochemical sensor for a chemical species, a micro-porous barrier to separate the or each electrochemical sensor from the environment of the module, the micro-porous barrier being of a material which is readily wetted by water, and electrolytic means for cleaning the micro-porous barrier.

The micro-porous barrier might be of electrically conducting material, for example micro-porous steel in the form of a membrane. In this case the cleaning means may comprise an electrically conducting mesh adjacent to the membrane but spaced apart from it, and means to provide a brief electrical voltage pulse between the mesh and the membrane, at intervals, so generating micro-bubbles by electrolysis which displace any fouling material from the surface of the membrane.

Alternatively the micro-porous barrier might be of a non-electrically conducting material, for example glass frit. In this case the cleaning means may comprise electrodes at either side of the barrier, and means to provide a brief electrical voltage pulse between the electrodes, at intervals, so generating micro-bubbles by electrolysis which flow through the glass frit and emerge at its exposed surface, dislodging any fouling material. The width of the micro-porous barrier separating the electrodes is desirably no more than 5 mm to ensure that the entire width of the surface is cleaned. The barrier might be in the form of an annulus, with concentric electrodes. A plurality of such barriers might be provided, separated from each other by electrodes, and the brief electrical pulses need only be provided between the outermost electrodes, as electrolysis will occur at the intervening electrodes which will act in a bipolar fashion.

The sensor module preferably comprises a plurality of non-liquid electrochemical sensors, for example a solid state pH electrode, a solid state chloride-ion sensing electrode, and a reference electrode. The module may also comprise a temperature sensor such as a platinum resistance thermometer. The reference electrode may comprise a second solid-state chloride-ion sensing electrode, coated with a gel or polymer containing a substantially constant concentration of chloride ions; this must be in electrical contact with the environmental liquids, but a mechanical barrier such as a perforated PTFE (Goretex) membrane or an impermeable barrier with a small hole may be provided to restrict diffusion of chloride ions away from the gel or polymer.

It will be appreciated that the electrolytically cleanable glass frit barrier described above could be used in other situations.

The invention will now be further and more particularly described, by way of example only, and with reference to the accompanying drawings, in which:

BRIEF DESCRIPTION OF THE DRAWINGS

Referring now to FIG. 1, a sensor module 10 comprises a cylindrical stainless-steel housing 12 open at each end and with an electrical connector 14 near one end, the lower end as shown. A circular ceramic plate 16 carrying sensor elements 18 (see FIG. 2) is glued into the housing 12 at the upper end as shown, and five wires 20 extend from the sensor elements 18 to the connector 14. The lower end of the housing 12 is sealed by a threaded stainless-steel base plate 22. Above the plate 16 and spaced apart from it by an insulating ring 24 is a cleaning module 25 consisting of a micro-porous steel membrane 26 above which is a steel mesh disk 27 separated by an insulating ring, the components of the module 25 being enclosed by an insulating sleeve, and being secured to the housing 12 by a threaded stainless-steel sleeve 28 with an internal lip. Wires 30 are spot welded to the membrane 26 and to the disk 27 respectively, and extend through holes in the housing 12 to the connector 14, passing outside the ceramic plate 16.

Referring now to FIG. 2, the plate 16 and the sensor elements 18 are shown in plan, the hatching indicating the elements 18, and the small circles 32 indicating the positions at which wires lead through the plate 16 to conductors on the rear surface which are connected to the wires 20 shown in FIG. 1. Each element 18 comprises a layer of platinum on the surface of the ceramic plate 16. One element 18a extends in a narrow arc near the periphery of the plate 16, forming an almost complete circle, and the resistance of this element 18a enables the temperature to be monitored. The other three elements 18b, c, d are in the form of sectors of a wider arc. In one element 18b the platinum is coated with pH glass, which has been annealed at 600° C., so providing a pH electrode. On the other two elements 18c and d, the platinum is coated with silver (by electrodeposition), and the outer surface of the silver is converted electrochemically to silver chloride. The element 18d is then coated with a layer of polymer (poly-(ethylene oxide)) containing lithium chloride; this element 18d acts as a reference element for the elements 18b and c.

Figure 1:
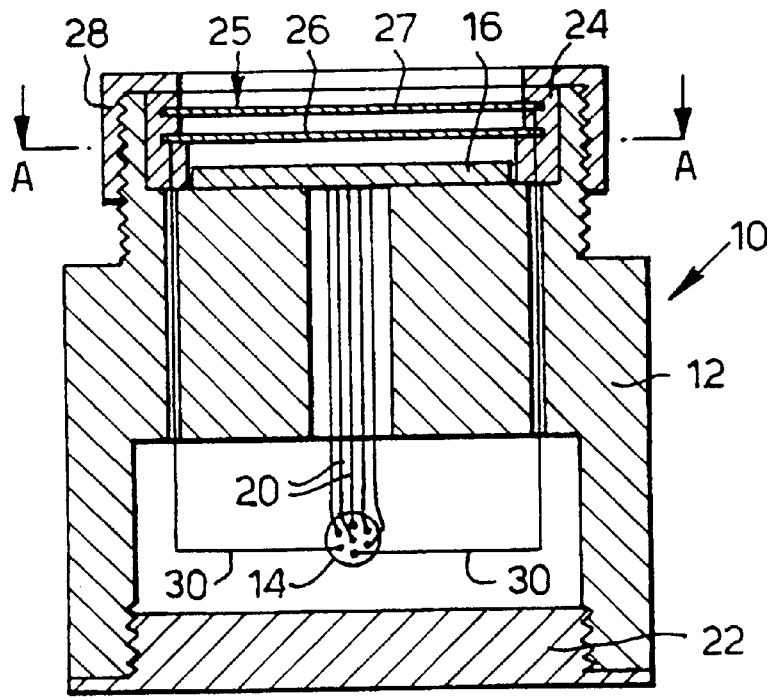
FIG. 1 shows a longitudinal sectional view through a sensor module.

Thus in use the resistance between the two ends of the element 18a enables the temperature to be measured. The voltage between the pH electrode 18b and the reference electrode 18d enables the pH of the aqueous phase to be determined. The voltage between the silver/silver chloride electrode 18c and the reference electrode 18d enables the concentration of chloride ions in the aqueous phase to be determined. Thus if the sensor module 10 is installed in an oil well, the connector 14 being connected to appropriate electronics, then the chemical nature of the aqueous phase in the oil well fluids can be monitored. The sensor elements 18 are protected from the oil phase in the oil well fluids by the micro-porous steel membrane 26; and at intervals (for example between 10 and 200 times a day) a voltage pulse is applied between the membrane 26 and the mesh 27, the electrical power supply being such that the current density is between 50 and 300 mA/cm² of membrane 25, such that bubbles are generated by electrolysis, so ensuring that any fouling material is dislodged.

At atmospheric pressure a pulse duration of about 5 s is usually found to be sufficient, but at higher pressure the bubbles are smaller, and a larger pulse has been found necessary. For example at 5000 psi (34 MPa) the pulse might be on for a minute, and at higher pressures the pulse would be longer still. The pulse duration may be adjusted in accordance with the pressure to which the module 10 is exposed.

Experimental tests have been carried out to investigate if the cleaning technique is effective at high pressures. One such test used a gold bead as test electrode, surrounded by, but separated from, a platinum ring counter electrode. These tests were carried out in a test cell containing simulated sea water, in which the pressure could be raised for example to 5000 psi (34 MPa). This pressure is about 340 times greater than atmospheric pressure, so that the gas bubbles generated during a cleaning pulse will have a volume about 340 times smaller than those generated in the same cell at atmospheric pressure. In order to monitor the state of the test electrode, the sea water also contained potassium ferricyanide and potassium ferrocyanide (each at 25 mM), which act as a redox couple. Cyclic voltammetry was then performed, sweeping the potential of the test electrode at 10 mV/s from zero to −100 mV to +100 mV and back to zero with respect to the counter electrode, and monitoring the current.

Figure 4:
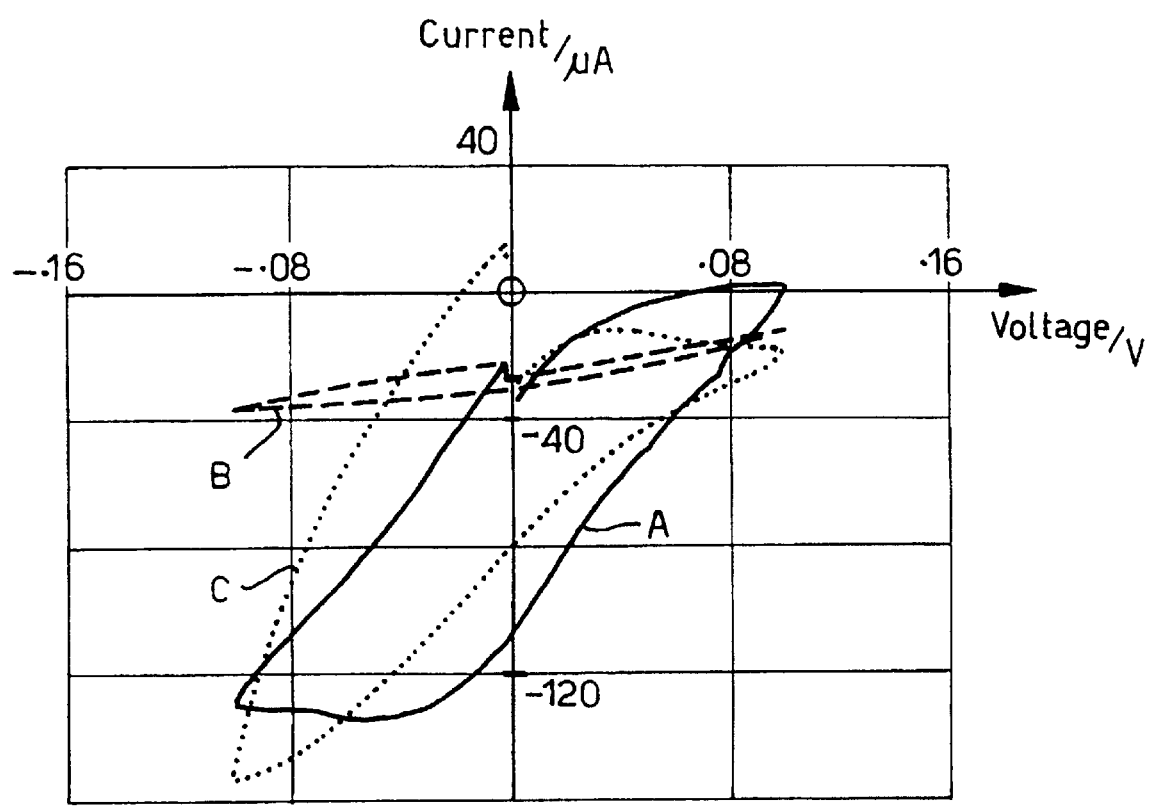
FIG. 4 shows graphically cyclic voltammograms for a test cell at a high pressure.

Referring now to FIG. 4 the current measurements during cyclic voltammetry are shown graphically in three different situations, all the measurements being taken at a pressure of 5000 psi. Graph A shows the results obtained with a clean test electrode. The test electrode was then removed from the cell, dipped in oil, and replaced in the cell; the graph B shows the results of cyclic voltammetry with the oiled test electrode after the pressure had been returned to 5000 psi. A cleaning pulse was then applied between the test electrode and the counter electrode; the graph C shows the results of cyclic voltammetry after cleaning the test electrode in this way. It is apparent from graph B that the presence of oil on the test electrode suppresses current flow during cyclic voltammetry, and it is apparent from graph C that the cleaning pulse is effective in markedly increasing the current flow during cyclic voltammetry (which indicates that the test electrode has been substantially cleaned).

Tests were also carried out using a 25 μm stainless-steel gauze test electrode and a platinum counter electrode, in a transparent test cell, at pressures up to 2000 psi (14 MPa). The potential difference required to attain a current of 200 MA/cm² was found to be substantially independent of the pressure. When the gauze was coated with oil, and pressure applied, there was no change in the potential difference required to cause such a current. A cloud of fine brown bubbles was observed to move out from the test electrode as the oil was displaced from its surface. At such a high pressure the bubbles are not buoyant enough to rise.

Figure 2:
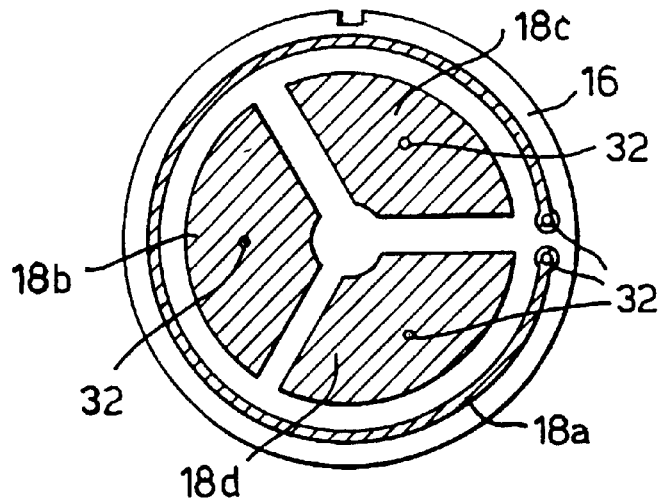
FIG. 2 shows a view on the line A—A of FIG. 1, showing only the sensor elements.

It will be appreciated that sensor module may differ from that described with reference to FIGS. 1 and 2 while remaining within the scope of the invention. For example the temperature sensing element 18a might be replaced with a thermocouple or a thermistor, which may be fabricated by screen printing using commercially available conductive inks. The reference electrode 18d might be covered with a different chloride-containing material, such as a gel, instead of a polymer. And both the reference electrode 18d and the silver/silver chloride electrode 18c might be further covered with an impermeable barrier film to suppress the leaching of chloride ions from the polymer (or the gel), and to suppress dissolution of silver chloride; this barrier film would have one or more apertures to ensure electrical contact with the aqueous phase of the liquids in the well.

Figure 3:
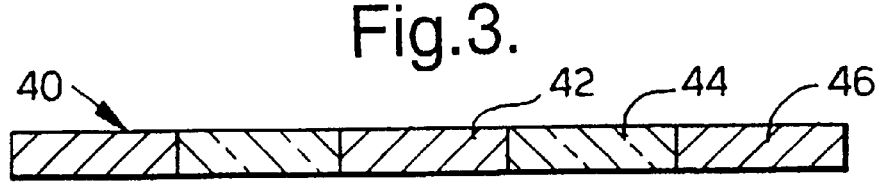
FIG. 3 shows a sectional view of an alternative barrier to that of FIG. 1.

In particular, the cleaning module 25 may be replaced with a different barrier. Referring now to FIG. 3, an alternative barrier is shown in section. The barrier 40 is circular and of overall diameter 20 mm. It consists of a central circular anode 42, a glass frit annulus 44 of radial width 4 mm, and a concentric outer annular cathode 46; the anode 42 and the cathode 46 are both of stainless-steel. The annulus 44 is permeable to fluids, although it is preferentially wetted by water. If it becomes fouled it can be cleaned by applying a brief pulse between the concentric electrodes 42 and 46 so that bubbles are generated in the frit (at the surfaces of the electrodes), flow through the frit annulus 44, and so restore an aqueous path.

Such a sensor module 10 may be incorporated in a probe to be lowered down an oil well, and can provide electrical signals from the sensors 18a–d via a cable to the surface. Alternatively a module 10 might be permanently installed downhole, for example in a recess in a pipe wall. Preferably any downhole probe would incorporate means to store electrical energy, and means to generate the cleaning pulses. The pulses may be applied at regular intervals, or in response to signals indicating the presence of contamination. The probe preferably also incorporates a pressure sensor, and the duration of the cleaning pulse is automatically adjusted in accordance with the pressure.

What is claimed is:

1. A method of sensing properties of an aqueous liquid at depth in an oil well, the oil well containing the aqueous liquid and an oil phase, the method comprising installing in the oil well an electrical sensor module, the module comprising at least one electrochemical sensor for a chemical species, and a micro-porous barrier to separate the or each electrochemical sensor from the environment of the module, the micro-porous barrier being of a material which is readily wetted by water, and electrolytic means for cleaning the micro-porous barrier, wherein the process also comprises applying a brief voltage pulse to the electrolytic cleaning means, at intervals.

2. A method as claimed in claim 1 wherein the micro-porous barrier is of electrically conducting material in the form of a membrane, and the cleaning means comprises an electrically conducting mesh adjacent to the membrane but spaced apart from it, and means to provide a brief electrical voltage pulse between the mesh and the membrane, at intervals.

3. A method as claimed in claim 1 wherein the micro-porous barrier is of a non-electrically conducting material, and the cleaning means comprises electrodes at either side of the barrier, and means to provide a brief electrical voltage pulse between the electrodes, at intervals.

4. A method as claimed in claim 3 wherein the width of the micro-porous barrier separating the electrodes is no more than 5 mm.

5. A method as claimed in claim 4 wherein the barrier is in the form of an annulus between concentric electrodes, the surface of the barrier that is exposed to the environment being an end surface of the annulus.

6. A method as claimed in claim 1 also comprising adjusting the operation of the electrolytic cleaning means in accordance with the pressure to which the module is exposed.

\* \* \* \* \*